United States Patent
Dor-Zidon

(10) Patent No.: US 10,835,705 B2
(45) Date of Patent: Nov. 17, 2020

(54) METAL-ORGANIC FRAMEWORK MATERIALS IN GASES DELIVERY SYSTEMS

(71) Applicant: Fisher & Paykel Healthcare Limited, Auckland (NZ)

(72) Inventor: Shahar Dor-Zidon, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 666 days.

(21) Appl. No.: 15/324,529

(22) PCT Filed: Jul. 10, 2015

(86) PCT No.: PCT/NZ2015/050089
§ 371 (c)(1),
(2) Date: Jan. 6, 2017

(87) PCT Pub. No.: WO2016/007025
PCT Pub. Date: Jan. 14, 2016

(65) Prior Publication Data
US 2017/0203073 A1    Jul. 20, 2017

Related U.S. Application Data

(60) Provisional application No. 62/022,931, filed on Jul. 10, 2014.

(51) Int. Cl.
*A61M 16/10* (2006.01)
*B01J 20/22* (2006.01)
(Continued)

(52) U.S. Cl.
CPC ...... *A61M 16/1075* (2013.01); *A61M 11/041* (2013.01); *A61M 11/042* (2014.02);
(Continued)

(58) Field of Classification Search
CPC .......... A61M 16/0891; A61M 16/0875; A61M 16/1075; A61M 16/104; A61M 16/105;
(Continued)

(56) References Cited

U.S. PATENT DOCUMENTS 3,837,337 A * 9/1974 LaViolette ............... A62B 7/08
128/205.12
5,360,002 A * 11/1994 Smith .................. A61M 16/22
128/205.12
(Continued)

FOREIGN PATENT DOCUMENTS

CA    2510863    10/2013
DE    3837139    8/1991

OTHER PUBLICATIONS

Robert Lemlich, Effect of Vibration on Natural Convective Heat Transfer, Jun. 1955, Department of Chemical Engineering University of Cincinnati, vol. 47 No. 6, pp. 1175-1180 (Year: 1955).*
(Continued)

*Primary Examiner* — Samchuan C Yao
*Assistant Examiner* — Margaret M Luarca
(74) *Attorney, Agent, or Firm* — Knobbe, Martens, Olson & Bear LLP

(57) ABSTRACT

A gases delivery system for medical use is disclosed that has a container configured to house a metal-organic framework material within at least one section of the container. An activation mechanism may be associated with the container. The metal-organic framework material may contain one or more substances such that the one or more substances may be released from the metal-organic framework material when energy is applied to the container via the activation mechanism. The activation mechanism may be a heating
(Continued)

mechanism. One or more containers housing metal-organic framework materials may be used in a gases recirculation system.

23 Claims, 6 Drawing Sheets

(51) Int. Cl.

| | | |
|---|---|---|
| *A61M 16/08* | (2006.01) | |
| *A61M 16/12* | (2006.01) | |
| *A61M 16/16* | (2006.01) | |
| *F17C 11/00* | (2006.01) | |
| *A61M 11/04* | (2006.01) | |
| *A61M 16/00* | (2006.01) | |
| *F17C 5/00* | (2006.01) | |
| *A61M 16/14* | (2006.01) | |
| *A61M 13/00* | (2006.01) | |

(52) U.S. Cl.
CPC ...... *A61M 16/024* (2017.08); *A61M 16/0875* (2013.01); *A61M 16/0891* (2014.02); *A61M 16/105* (2013.01); *A61M 16/109* (2014.02); *A61M 16/12* (2013.01); *A61M 16/16* (2013.01); *B01J 20/226* (2013.01); *F17C 5/00* (2013.01); *F17C 11/00* (2013.01); *A61M 13/003* (2013.01); *A61M 16/142* (2014.02); *A61M 16/161* (2014.02); *A61M 2016/0027* (2013.01); *A61M 2016/0033* (2013.01); *A61M 2202/025* (2013.01); *A61M 2202/0208* (2013.01); *A61M 2202/0225* (2013.01); *A61M 2202/0241* (2013.01); *A61M 2202/0266* (2013.01); *A61M 2202/0283* (2013.01); *A61M 2205/02* (2013.01); *A61M 2205/12* (2013.01); *A61M 2205/123* (2013.01); *A61M 2205/127* (2013.01); *A61M 2205/3331* (2013.01); *A61M 2205/3368* (2013.01); *A61M 2205/584* (2013.01); *A61M 2205/8206* (2013.01); *F17C 2201/0138* (2013.01); *F17C 2250/03* (2013.01); *F17C 2270/025* (2013.01); *Y02C 20/10* (2013.01)

(58) Field of Classification Search
CPC .... A61M 16/12; A61M 16/16; A61M 11/042; A61M 11/041; A61M 16/109; A61M 16/142; A61M 16/161; A61M 13/003; A61M 2016/0027; A61M 2016/0033; A61M 13/00; A61M 16/22; A61M 16/024; B01J 20/226; F17C 5/00; F17C 11/00; B01D 2253/204; B01D 2259/4525; B01D 2259/4541; B01D 53/0415; A62D 9/00; C25B 3/12; Y10S 95/90
USPC .................................................. 128/206.26
See application file for complete search history.

(56) References Cited

U.S. PATENT DOCUMENTS

| | | | |
|---|---|---|---|
| 7,736,132 | B2 | 6/2010 | Bliss et al. |
| 8,118,769 | B2* | 2/2012 | Diemunsch .......... A61M 11/041 604/23 |
| 8,876,953 | B2* | 11/2014 | Yaghi ..................... B01D 53/02 502/401 |
| 2003/0101996 | A1* | 6/2003 | Franberg ............ B01D 53/0446 128/205.12 |
| 2004/0118286 | A1 | 6/2004 | Bretovansky |
| 2009/0032023 | A1* | 2/2009 | Pastre ..................... A62D 9/00 128/205.28 |
| 2011/0104213 | A1 | 5/2011 | Rosi et al. |
| 2011/0277767 | A1* | 11/2011 | Yaghi ..................... B01D 53/02 128/205.27 |
| 2013/0025591 | A1 | 1/2013 | Clark et al. |
| 2014/0260977 | A1* | 9/2014 | Kwon .................. B01J 20/048 95/106 |

OTHER PUBLICATIONS

Yun-Nan Gong and Tong-Bu Lu, Fast detection of oxygen by the naked eye using a stable metal—organic framework containing methyl viologen cations, Jul. 22, 2013, The Royal Society of Chemistry, Chem. Commun. 2013 / 49, pp. 7711-7713 (Year: 2013).*

Extended Search Report for EP Application No. 19185054.4 dated Jan. 17, 2020, 8 pages.

* cited by examiner

METAL-ORGANIC FRAMEWORK MATERIALS IN GASES DELIVERY SYSTEMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority benefit of U.S. Provisional Application No. 62/022,931, filed Jul. 10, 2014, the entirety of which is hereby incorporated by reference herein.

BACKGROUND

Technical Field

The present disclosure generally relates to apparatus and methods for delivering conditioned gases to a patient. More particularly, the present disclosure relates to apparatus and methods for storing substances, such as gases and/or vapour, in a metal-organic framework material such that the substances can be delivered to a patient.

Description of the Related Art

Gases such as air, oxygen, nitrous oxide, or carbon dioxide can be delivered to a patient by a gases delivery system. The gases may be conditioned to improve the efficacy of the treatment to the patient, where conditioning may include heating and/or humidification of the gases. A laparoscopic system may supply carbon dioxide to the peritoneum of the patient. Humidified gases in a laparoscopic system help to reduce damage caused by cold, dry surgical gases during surgery by enabling the peritoneum to remain moist and warm. Humidified gases can also help to reduce damage caused by cold, dry surgical gases during open surgery. This may have a positive effect on post-operative pain and may cause a reduction in recovery time for patients.

A humidification system may use gases that are supplied from a gases source such as an insufflator and may use pass-over humidification to condition the gases. Pass-over humidification uses a humidification chamber containing a liquid, such as water, that is heated via a heating element. The vapour generated by the liquid is taken up by the gases as the gases travel through the humidification chamber and to the patient.

The liquid in the humidification chamber may splash the user or circuit, or may tip out if the humidification chamber is tilted. The liquid may also cause the humidification chamber to be heavy. Thus, the portability of the humidification chamber may be limited.

Systems have been developed that atomise or nebulise liquid water to be provided to the patient; however, these systems can be expensive and cumbersome and may be easily contaminated if handled incorrectly. The spray produced by such a system may result in wet, cold gas being delivered to the patient rather than heated, vapor-laden gas.

Lean amines with high selectivity to carbon dioxide can be used as gas separators. They may come in a solution form with water stored as a liquid. Storing water in the liquid form, however, may reduce the capacity of the system and make the system highly corrosive.

SUMMARY

A system is disclosed that uses a metal-organic framework material to store gases prior to delivery to the patient. The metal-organic framework material may be chosen such that it has a high selectivity to carbon dioxide, oxygen, nitrous oxide, argon, nitrogen, helium, vapour, such as water vapour, and/or medicaments. A normally undesirable property of the metal-organic framework material is that absorption of vapour may occur from the surrounding environment. This property, however, can also be used to store substances to provide vapour and/or conditioned gases to the patient. The application of energy, for example in the form of heat, to the metal-organic framework material may cause the gases and/or vapour to be released from the metal-organic framework material, providing conditioned gases that may be delivered to the patient.

The system therefore may not require a volume of a liquid, such as water, because the water may be stored as vapour in a solid state rather than a liquid state within a container. Thus, the orientation of the container may not affect usage of the device, and splashing or tipping out of the liquid may be reduced when the device is tilted or moved. The system may enable specific application of energy to generate a precise amount of vapour and/or gases at a particular time.

By storing the vapour in this way, the capacity of the system may be improved and the system may be less vulnerable to corrosion. The system may be compact and thus may be more portable and more easily handled than prior gases conditioning systems. Thus, the system may be more readily incorporated into gases delivery systems, such as laparoscopic or respiratory systems.

An embodiment is disclosed that may use a metal-organic framework material that is preloaded with one or more substances such that the one or more substances can be released in use.

An embodiment is disclosed that may preload one or more metal-organic framework materials housed in different containers, or different sections of a container, with one or more substances such that energy can be applied to selected containers or sections to release the desired composition of the one or more substances at that time.

An embodiment is disclosed that may preload a metal-organic framework material housed in a container with vapour, such as water vapour, such that heating the container releases the vapour from the metal-organic framework material and into a gases flow, thereby conditioning the gases flow as it passes through the system.

According to at least one aspect of the present disclosure, a gases delivery system for medical use can have one, some, or all of the following features, as well as other features described herein. The gases delivery system comprises a gases source configured to supply gases. The gases delivery system comprises a patient interface configured to be in fluid communication with the gases source. The patient interface is configured to deliver the gases to a patient. The gases delivery system comprises a container having an outlet configured to be in fluid communication with the patient interface. The container is configured to house a metal-organic framework material. The metal-organic framework material is configured to store and release at least one substance. The gases delivery system comprises an activation mechanism configured to apply energy to the metal-organic framework material to cause the metal-organic framework material to release the at least one substance.

The metal-organic framework material can be preloaded with the at least one substance. The metal-organic framework material can be rechargeable with the at least one substance. The at least one substance can comprise one or more of vapour, such as water vapour, carbon dioxide, oxygen, nitrous oxide, argon, nitrogen, helium, or at least one medicament. The metal-organic framework material can comprise one or more of pellets, a powder, a mesh, a box, a monolith, or a lattice. The gases source can be located in the container. The gases source can be an external gas supply. The container can comprise an inlet configured to be in fluid communication with the gases source. The external gas supply can be configured to supply heated gases. The external gas supply can be configured to supply humidified gases. The external gas supply can be one of a gases canister, insufflator, ventilator, blower, or wall source.

The gases delivery system can comprise a gas permeable membrane covering the inlet. The gas permeable membrane covering the inlet can be configured to prevent the metal-organic framework material escaping the container through the inlet. The gases delivery system can comprise a gas permeable membrane covering the outlet. The gas permeable membrane covering the outlet can be configured to prevent the metal-organic framework material escaping the container through the outlet. The container can comprise a plurality of sections. Each section can house a metal-organic framework material. At least two of the plurality of sections can house different metal-organic framework materials. At least two of the plurality of sections can house similar amounts of the same metal-organic framework material. At least two of the plurality of sections can house different amounts of the same metal-organic framework material. Each of the plurality of sections can comprise an activation mechanism. The activation mechanisms of at least two of the sections can be operated independently of each other.

The container can comprise a tube. The tube can comprise a wall. The wall can comprise at least a portion of the metal-organic framework material. The container can comprise a transparent section. The transparent section can allow a user to view a change in a level of the at least one substance stored in the metal-organic framework material. The metal-organic framework material can change color in response to a change in the level of the at least one substance stored in the metal-organic framework material. The transparent section can allow a user to view changes in the color of the metal-organic framework material.

The activation mechanism can be disposed within the container. The activation mechanism can be part of the container. The activation mechanism can be external to the container. The activation mechanism can be configured to provide heat energy. The activation mechanism can be configured to provide heat and vibration energy. The activation mechanism can be a preheated gas flow directed into the container. The activation mechanism can be configured to be manually controlled by a user. The activation mechanism can be configured to be controlled by a control system. The container can be configured to be disposed in-line between the gases source and the patient interface. The container can be configured to be coupled to the patient interface via a circuit. The circuit can comprise a first end configured to be coupled to the outlet of the container and a second end configured to be coupled to the patient interface.

According to at least one aspect of the present disclosure, a method for preloading a metal-organic framework material with at least one substance can have one, some, or all of the following features, as well as other features described herein. The method for preloading a metal-organic framework material comprises providing the metal-organic framework material in a container, starting a flow of a gas into the container, stopping the flow of the gas into the container, and sealing the container. The flow of the gas into the container carries the at least one substance into the metal-organic framework material in a vapour form.

The method for preloading a metal-organic framework material can comprise, prior to starting the flow of the gas into the container, applying energy to the metal-organic framework material. The flow of the gas into the container can be stopped when a selected amount of time has elapsed after the flow of the gas into the container was started. The gas can flow into the container under pressure. The container can comprise an inlet and an outlet. The gas can flow into the container through the inlet. The gas can flow out of the container through the outlet. The diameter of the inlet is larger than the diameter of the outlet.

The method for preloading a metal-organic framework material can comprise measuring the pressure of the gas within the container. The flow of the gas into the container can be stopped when the pressure reaches a selected pressure. Applying energy to the metal-organic framework material can comprise applying heat energy to the metal-organic framework material. Applying energy to the metal-organic framework material can comprise applying heat and vibration energy to the metal-organic framework material. The metal-organic framework material can be selective to the gas. The metal-organic framework material can be non-selective to the gas.

According to at least one aspect of the present disclosure, a gases recirculation system for medical use can have one, some, or all of the following features, as well as other features described herein. The gases recirculation system comprises a container. The container houses a metal-organic framework material. The metal-organic framework material is configured to store and release at least one substance. The container comprises a recovery inlet configured to receive recirculated gases. The gases recirculation system comprises a recovery circuit. The recovery circuit is configured to be coupled to the recovery inlet. The recovery circuit is configured to deliver the recirculated gases to the recovery inlet. The gases recirculation system comprises a filter. The filter is configured to filter the recirculated gases.

The container can comprise a plurality of sections of the metal-organic framework material. The gases recirculation system can comprise a plurality of containers each housing metal-organic framework materials.

For purposes of summarizing the disclosed systems and apparatus, certain aspects, advantages and novel features of the disclosed systems and apparatus have been described herein. It is to be understood that not necessarily all such advantages may be achieved in accordance with any particular embodiment of the disclosed systems and apparatus. Thus, the disclosed systems and apparatus may be embodied or carried out in a manner that achieves or optimizes one advantage or group of advantages as taught herein without necessarily achieving other advantages as may be taught or suggested herein.

BRIEF DESCRIPTION OF THE DRAWINGS

The disclosed apparatus and systems will now be described with reference to the following figures which are intended to illustrate and not to limit the preferred embodiments.

DETAILED DESCRIPTION

Figure 1:
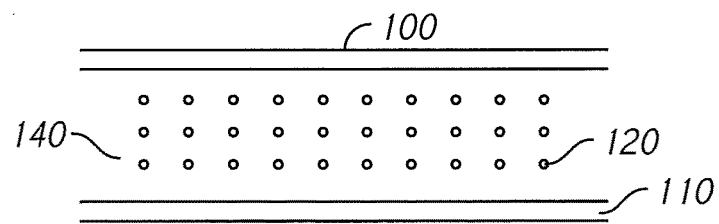
FIGS. 1-4 are cross-sectional top views of a container comprising a metal-organic framework material according to embodiments of the present disclosure.

A container as herein described may refer to, for example, a canister, cartridge, chamber, or tube, wherein the canister, cartridge, chamber, or tube is configured to hold one or more substances and may be in gaseous or fluid communication with a gases supply and/or a patient interface. It is to be understood that variations or modifications may still be within the scope of the disclosed apparatus and systems.

A gases source as herein described may refer to, but is not limited to, a gases canister, an insufflator, a ventilator, a blower, or a wall supply, for example.

An activation mechanism as herein described may refer to a mechanism for releasing molecules from a metal-organic framework material. Activation mechanisms can include, for example, heating mechanisms or heating and vibration mechanisms. A heating mechanism as herein described may refer to, for example, at least one heater wire, at least one heating filament, at least one heater element, or other ways of heating.

A substance or substances as herein described may refer to, for example, gases, such as carbon dioxide, oxygen, nitrous oxide, argon, nitrogen, helium, and/or vapour, such as but not limited to, water vapour, or volatiles, such as medicaments or anaesthetics.

A patient interface as herein described may refer to, for example, a face mask, endotracheal tube, nasal cannula, nasal mask, oral mask, tracheal mask, laparoscopic cannula, or diffuser.

A circuit as herein described may refer to, for example, a tube, conduit, or gases transportation pathway.

In-line as herein described may refer to a component that fits within a circuit or other aspect of a gases delivery system such that the component does not need additional external electrical and/or pneumatic connections over those required to connect the circuit with the system. The in-line component may be lightweight and may not require additional support, such as anchoring on a surface. Thus, the in-line component may have improved flexibility and portability within the gases delivery system.

A mixture as herein described may refer to a substantially homogeneous combination of substances that has substantial uniformity or may be sufficiently mixed. The mixture may comprise different concentrations of the substances as desired by a user.

A metal-organic framework material as herein described may refer to clusters of metal ions that may be coordinated to form a porous structure that can be used for storage of one or more substances. The structure may be provided in the form of one or more of pellets, a powder, a mesh, a box, a monolith, or a lattice, and may comprise a mixture of the metal-organic framework material with different structures such that the selectivity of the material can be specified. The pellets may comprise a mixture or in some cases may comprise stacked individual layers of the metal-organic framework material with different structures. Other forms of metal-organic framework materials may also be envisioned, without limitation, by the embodiments disclosed herein.

Referring to FIG. 1, an example embodiment of a container 100 comprises a metal-organic framework material 120 within a body 140 of the container 100. In some embodiments, the container 100 comprises an activation mechanism 110, such as a heating mechanism. The activation mechanism 110 may be integral or embedded in a wall of the container 100. Alternatively, the activation mechanism may be separate from and/or external to the container 100. The activation mechanism 110 may, for example, heat the container 100 in use. The metal-organic framework material 120 is configured to receive and store one or more substances, such as, for example, one or more medicaments, carbon dioxide, other gases, vapour or a mixture of any of the above. The container 100 is preloaded with one or more substances, which are stored by the metal-organic framework material 120. The application of energy to the container 100 via the activation mechanism 110 causes the metal-organic framework material 120 to release the one or more stored substances, which can then be transported to a patient. In some embodiments, a mixture of multiple substances, such as, for example but not limited to, carbon dioxide and water vapour, may be released that may comprise a ratio of such substances that is useful for therapeutic use.

In other embodiments, other mechanisms instead of or in addition to a heating mechanism can be used as the activation mechanism 110 to release a substance from the metal-organic framework material 120. For example, a substance can be released from the metal-organic framework material 120 by heating and vibration. In some embodiments in which vibration or another mechanism is used to release a substance in addition to heat, less heat may be needed to release the substance.

In some embodiments, an outer housing or shell of the container 100 is transparent, or at least partially transparent, or includes a transparent, or at least partially transparent, section. Some types of the metal-organic framework material 120 change color upon the addition or removal of a particular substance to or from the metal-organic framework material 120. For example, some types of the metal-organic framework material 120 change from dark blue to light blue upon the removal of humidity or vapour. The transparent housing or section allows a user to view such a color change.

Figure 2:
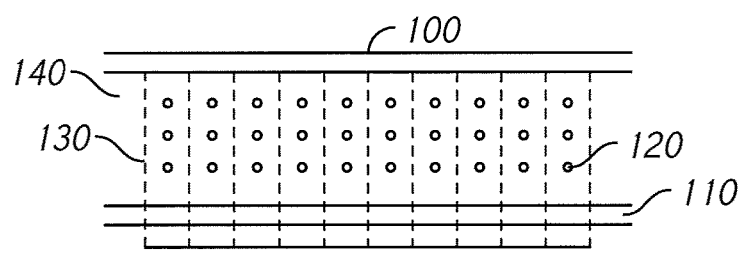
Figure 3:
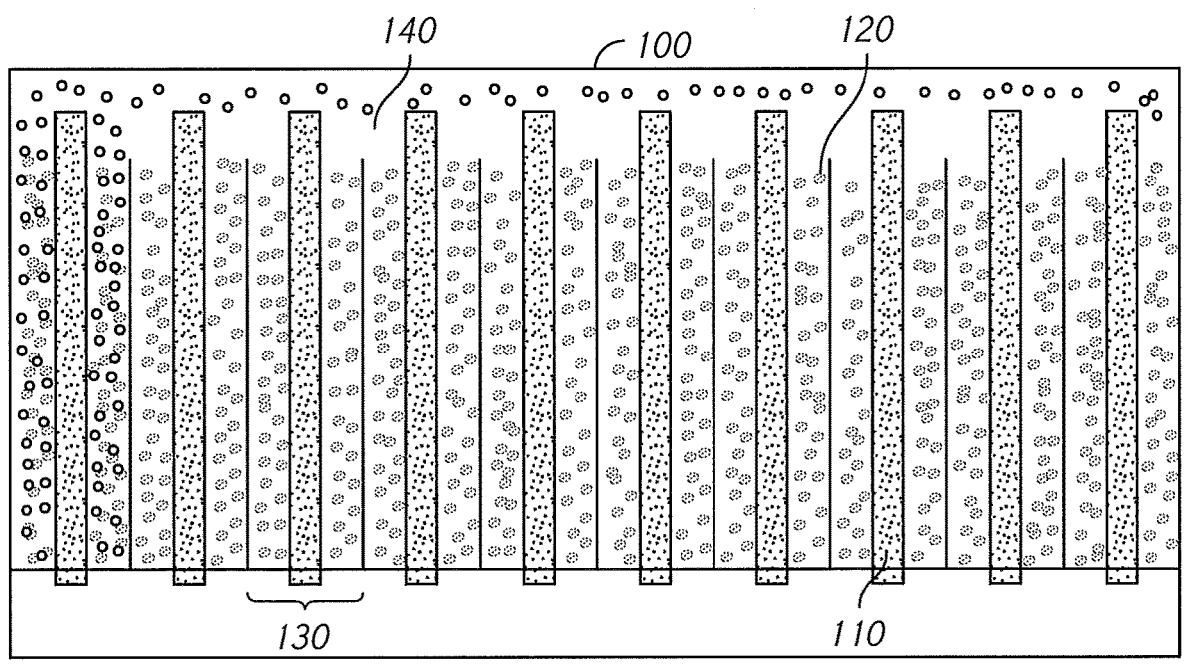

FIGS. 2 and 3 show the container 100 with sections 130 defining portions of the metal-organic framework material 120 that have been loaded with one or more substances. Energy can be differentially applied to the sections 130 via the activation mechanism 110 such that different amounts of the one or more substances can be released from the metal-organic framework material 120. A user may independently control the heat and/or other energy that is applied to the sections 130 to control the treatment. In some embodiments, an intelligent feedback loop or control system may control the activation mechanism 110 as described in greater detail herein. In some embodiments, each of the sections 130 includes its own one of the activation mechanism 110. For example, in the embodiment of FIG. 3, each of the sections 130 includes its own one of the activation mechanism 110, such as a heating wire or filament. In other embodiments, multiple of the sections 130 can share a common one of the activation mechanism 110, and the activation mechanism 110 can be selectively controlled and activated, either manually or via a control system, to apply energy to only a selected one or more of the sections 130 at a given time.

In some embodiments, one or more of the sections 130 can be separately removed from, replaced, and/or recharged (meaning additional substances can be loaded into the metal-organic framework material 120) from other of the sections 130. For example, in some embodiments, the container 100 can include one or more removable cartridges each containing one or more of the sections 130. The cartridge(s) can be selectively removed, replaced, and/or recharged as needed or desired. In some such embodiments, one or more of the sections 130 includes its own one of the activation mechanism 110. The one or more of the activation mechanism 110 can be included in the removable cartridge(s) or can remain in the container 100. In other embodiments, one or more of the sections 130 can share a common one of the activation mechanism 110 that remains in the container 100 as various ones of the sections 130 are removed and/or replaced, and portions of the activation mechanism 110 can be selectively activated to differentially apply energy to different ones of the sections 130. In some embodiments, the metal-organic framework material 120 in different ones of the sections 130 can be loaded with different substances.

In use, the one or more of the activation mechanism 110 can be selectively or differentially activated to selectively release substances from different ones of the sections 130. If a greater amount of a particular substance or substances is needed or used during the course of a procedure or treatment, the one or more of the sections 130 or cartridges containing that substance can be removed and recharged or replaced with other of the sections 130 or cartridges pre-loaded with that substance. In some embodiments, the separability of the one or more of the sections 130 or cartridges can allow for optional additional substances, for example, oxygen or one or more medicaments, to be added to the container 100 to customize the container 100 for a particular patient, procedure, or treatment or to add optional additional substances to the container 100 if the need arises during the procedure or treatment.

Figure 4:
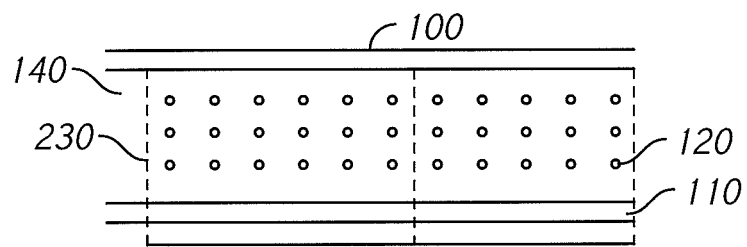

Referring to FIG. 4, an embodiment is shown wherein the container 100 comprises sections 230. The sections 230 may be preloaded with one or more substances such as carbon dioxide, other gases, medicaments, and/or vapour as above. However, in this embodiment each of the sections 230 may comprise only one substance. For example, a first of the sections 230 may comprise carbon dioxide and a second of the sections 230 may comprise vapour, such as water vapour. Thus, if energy is applied differentially via the activation mechanism 110 as in the previous embodiment, the released substances may vary considerably. For example, in some cases, energy may be applied via the activation mechanism 110 to one of the sections 230 comprising carbon dioxide, which may release only the carbon dioxide contained within that one of the sections 230. Similarly, energy may be applied via the activation mechanism 110 to one of the sections 230 comprising vapour and, thus, the vapour within that one of the sections 230 may be released. In some cases, the activation mechanism 110 may be controlled such that energy may be applied to a portion of one of the sections 230, or such that energy may be applied to a number of the sections 230 or a number of portions of the sections 230, thereby allowing a user to have fine control of the proportion of the substances that are released. In some embodiments, for example as shown in FIG. 4, multiple of the sections 230 share a common one of the activation mechanism 110 and different portions of the activation mechanism 110 can be selectively activated to differentially apply energy to different ones of the sections 230. In other embodiments, one or more of the sections 230 can each include their own one of the activation mechanism 110.

As described with respect to FIGS. 2 and 3, in some embodiments, one or more of the sections 230 can be separately removed from, replaced, and/or recharged from other of the sections 230. For example, in some embodiments, the container 100 can include one or more cartridges containing one or more of the sections 230. The cartridge(s) can be selectively removed, replaced, and/or recharged as needed or desired, as described with respect to FIGS. 2 and 3.

Figure 5:
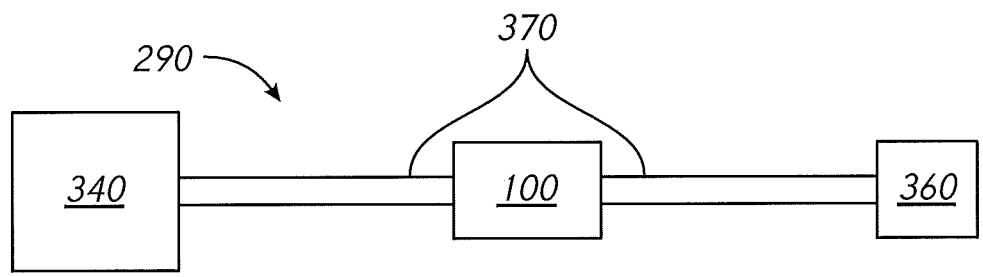
FIG. 5 is a schematic of a system comprising a container that comprises a metal-organic framework material according to an embodiment of the present disclosure.

Referring to FIG. 5, a gases delivery system 290 comprises a gases source 340, the container 100, a circuit 370, and a patient interface 360. In the illustrated embodiment, the container 100 is configured to be in-line with the gases delivery system 290. The patient interface 360 can be, for example, an interface configured to deliver respiratory gases to the patient, such as, for example, a face mask, endotracheal tube, nasal cannula, nasal mask, oral mask, or tracheal mask, or an interface configured to deliver insufflation gases to the patient during surgical procedures, such as, for example, a laparoscopic cannula or diffuser. The container 100 is configured to be a humidification device that comprises the metal-organic framework material 120 and the activation mechanism 110. In the illustrated embodiment, the activation mechanism 110 is a heating mechanism. The metal-organic framework material 120 in the container 100 may be preloaded with a substance such as water vapour. A gases flow may pass through the circuit 370 and reach the container 100. As the gases flow passes through the container 100, energy may be applied via the activation mechanism 110, which may heat the container 100 such that water vapour is released from the metal-organic framework material 120. The gases flow may be in contact with the released water vapour such that the gases flow is humidified as it passes through the container 100. The humidified gases can then be delivered to the patient through the patient interface 360.

The container 100, or more specifically the activation mechanism 110 of the container 100, can receive power from another component of the gases delivery system 290, such as the gases source 340, or from an external or internal power source, such as a battery. In some embodiments, the gases source 340 can supply preheated and/or prehumidified gases. In some such embodiments, preheated gases act as the activation mechanism 110 and cause the water vapour or other substances stored in the metal-organic framework material 120 to be released from the metal-organic framework material 120 as the preheated gases flow through the container 100.

In some embodiments, the container 100 can be integrated with the gases source 340, or the gases source 340 and the container 100 can be co-located in the same housing. In some embodiments, the container 100 can be coupled to or integrated with the patient interface 360. In some embodiments, the circuit 370, or at least the portion of the circuit 370 extending between the container 100 and the patient interface 360, is heated and/or insulated to reduce the formation of condensate in the circuit 370.

In some embodiments, the circuit 370 can include a pressure management system (not shown) to ensure that desired pressure levels are maintained at the patient interface 360. Such a pressure management system can include, for example, a gases reservoir, a pressure regulator, a valve, a filter, and/or a controller. An example embodiment of a gases delivery system comprising such a pressure management system is disclosed in International Patent Publication No. WO 2014/112886, published 24 Jul. 2014, the entirety of which is herein incorporated by reference.

In some embodiments, the metal-organic framework material 120 can also or alternatively be loaded with one or more volatile medicaments. The activation mechanism 110 applies energy to release the medicaments from the metal-organic framework material 120, and the medicaments can be delivered to the patient through the patient interface 360.

In some embodiments, the container 100 is or includes a tube, such as the circuit 370. For example, instead of or in addition to the container 100 being a separate component of the gases delivery system 290, part or all of the circuit 370 can include the metal-organic framework material 120. For example, in some embodiments, at least part of a wall of the circuit 370 includes or is made of the metal-organic framework material 120.

Figure 6:
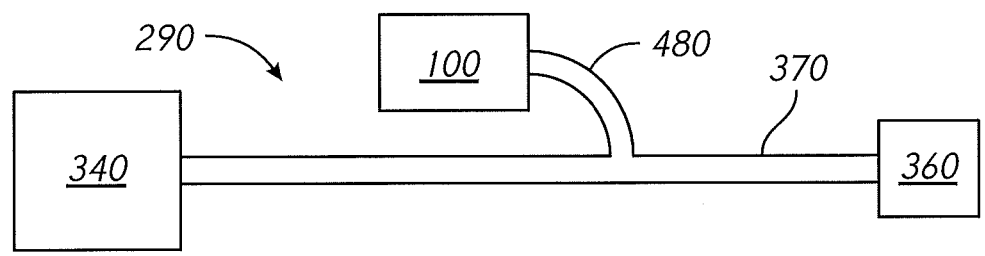
FIG. 6 is a schematic of a gases delivery system according to an embodiment of the disclosure.

FIG. 6 shows a variant of the embodiment shown in FIG. 5. In FIG. 6, the container 100 is not in direct contact with the gases flow through the circuit 370. Rather, the container 100 comprises or is configured to connect to a connection tube 480 that connects to the circuit 370 and allows a passage of vapour from the container 100 into the gases flow in the circuit 370. The gases flow may take up the vapour as it passes through the circuit 370. Thus, the gases flow can be humidified by the vapour generated from the container 100 and can be delivered to the patient via the patient interface 360.

Figure 7:
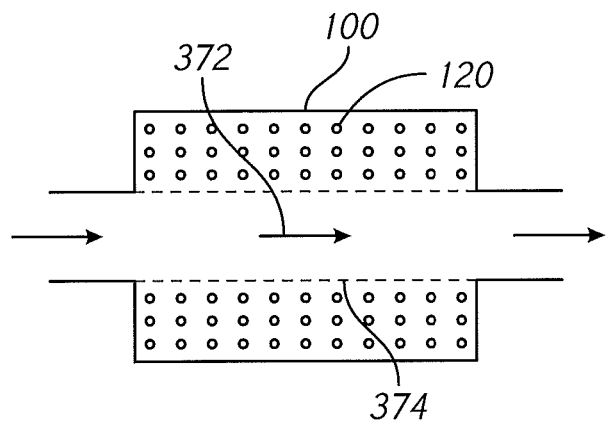
FIG. 7 is a schematic of a container comprising a metal-organic framework material according to an embodiment of the disclosure.

FIG. 7 shows an example embodiment of the container 100, which can be, for example, a canister or tube, wherein the metal-organic framework material 120 is contained in the wall of the container 100 or in a portion of the container 100 defining and/or surrounding a flow path 372 through the container 100. The metal-organic framework material 120 can be loaded with a substance, such as vapour, $CO_2$ and/or other gases, and/or volatile medicament(s). In addition, gases, such as, for example, $CO_2$, can be passed through the flow path 372. In some embodiments, the container 100 includes a built-in one of the activating mechanism 110, such as a built-in heating mechanism. The container 100 can include a gas permeable layer 374 surrounding the flow path 372 between the metal-organic framework material 120 and the flow path 372. The gas permeable layer 374 inhibits or reduces the likelihood of the metal-organic framework material 120 escaping from the container 100 while allowing the substance, such as gas(es) or volatile medicament(s), to pass through the gas-permeable layer 374 into the flow path 372. In some embodiments, the gas permeable layer 374 is selectively permeable to the substance when released from the metal-organic framework material 120 but not permeable to, for example, $CO_2$ or another gas that is passed through the flow path 372, so that the $CO_2$ or the other gas remains in the flow path 372.

Figure 8:
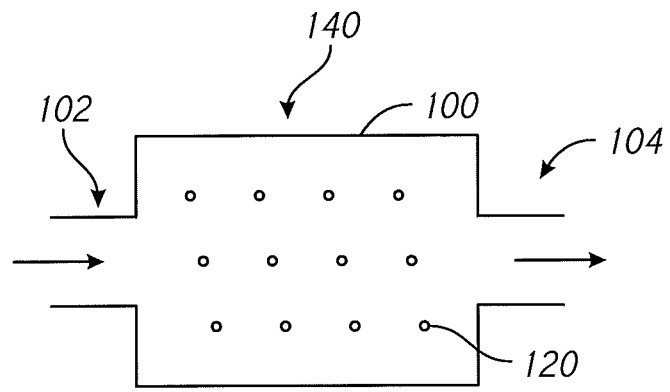
FIG. 8 is a schematic of a container comprising a metal-organic framework material according to an embodiment of the present disclosure.
Figure 9:
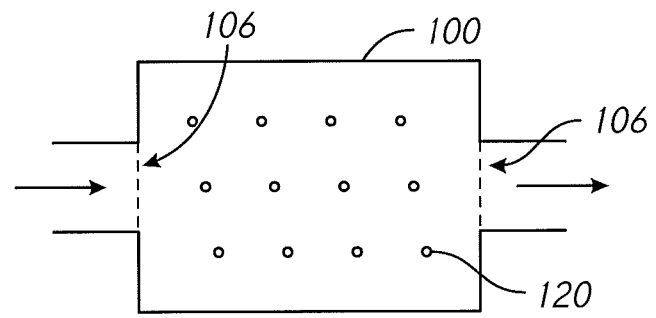
FIG. 9 is a schematic of a container comprising a metal-organic framework material according to an embodiment of the present disclosure.

In some embodiments, for example as shown in FIG. 8, an inlet 102 and/or an outlet 104 of the container 100 are relatively small (e.g., compared to the body 140 of the container 100) to help inhibit or prevent the metal-organic framework material 120 from escaping the container 100. In some embodiments, for example as shown in FIG. 9, the inlet 102 and/or the outlet 104 can include or be covered by a gas-permeable membrane or mesh 106 to help inhibit or prevent the metal-organic framework material 120 from escaping or moving through the inlet 102 and/or the outlet 104.

The metal-organic framework material 120 according to the present disclosure can be provided in the form of, for example, one or more of pellets, a powder, a mesh, a box, a monolith, or a lattice. Gases passing through the metal-organic framework material 120 are exposed to a tailored surface area of the stored substances. In some embodiments, the form of the metal-organic framework material 120 can affect the surface area exposed to the gases. For example, a form such as a mesh shape or pellets can provide a tortuous path through the metal-organic framework material 120 for the gases. If the container 100 contains a smaller available surface area of the metal-organic framework material 120, then more energy, e.g., heat, may be required to release the stored substances into the gases flowing through the container to achieve the desired concentration of the substances in the gas flow. Therefore, a larger surface area may reduce the energy needed. However, the metal-organic framework material 120 having a larger surface area may also take up more space. Therefore, the size and/or shape or the metal-organic framework material 120 can be selected to optimize surface area based on considerations of space and energy usage. The size of the metal-organic framework material 120 can also be selected based on considerations of the amounts of the particular substances needed to be stored for the particular intended use for the patient and the amounts of those particular substances that the metal-organic framework material 120 can hold per volume or weight of the material. For example, in some embodiments, the metal-organic framework material 120 can hold 100 liters of $CO_2$ per kilogram.

The exposed surface area of the metal-organic framework material 120 can also be selected for dose control. In other words, the exposed surface area can be selected to help control the amount of the stored substances released from the metal-organic framework material 120 in a given time period. Dose control can be particularly important when the substances includes one or more medicaments that may be more beneficial to the patient if released over a longer period of time and/or that may be expensive such that it may be beneficial to reduce the total amount used during a particular procedure, for example, to the lowest beneficial dose.

In some embodiments, it may be beneficial to deliver gases with a combination of medicaments, humidity (e.g., water vapour), and/or $CO_2$ or other gases to the patient. Medicaments, humidity, and/or $CO_2$ or other gases can be added to a gas flow delivered to a patient in various ways. For example, in some embodiments, $CO_2$ or other gases, vapour, and one or more medicaments are all stored in one or more of the metal-organic framework material 120 and released from the one or more of the metal-organic framework material 120 by the activation mechanism 110 to be delivered to the patient. In some embodiments, the gases delivery system 290 can include multiple of the container 100, each including one or more substances, such as medicaments, humidity, and $CO_2$ or other gases. In some embodiments, the container 100 can include multiple sections or cartridges containing different substances, as described in greater detail herein. In some embodiments, one or more of the metal-organic framework material 120 store one or more medicaments and humidity, and $CO_2$ or other gases is flowed through the one or more of the metal-organic framework material 120. The $CO_2$ or other gases flowing through the one or more of the metal-organic framework material 120 can be heated and/or the container 100 can include a heating element to heat the gases passing through and leaving the container 100 and release the substances stored in the one or more of the metal-organic framework material 120. In other embodiments, one or more of the metal-organic framework material 120 can store one or more medicaments, and heated and humidified $CO_2$ or other gases can be flowed through the material(s).

Figure 10:
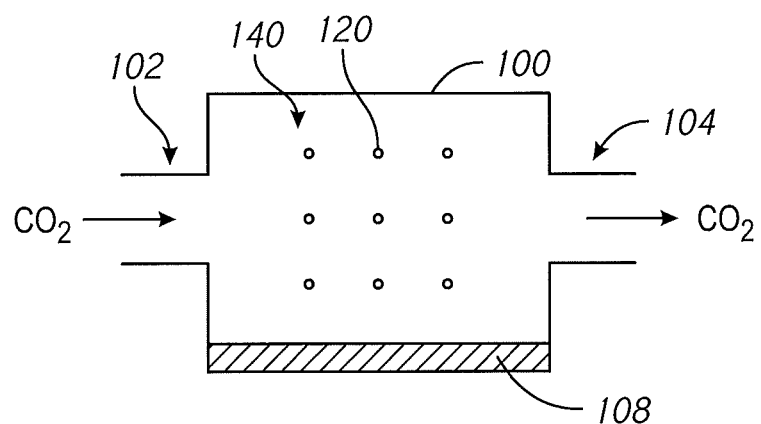
FIG. 10 is a schematic of a container comprising a metal-organic framework material and a humidification system according to embodiments of the present disclosure.

FIG. 10 illustrates an example embodiment of a system for storing one or more medicaments and delivering the medicaments to a patient. As shown, the container 100 includes the inlet 102, the outlet 104, the body 140 housing the metal-organic framework material 120, and a humidification system 108. The metal-organic framework material 120 stores one or more medicaments. $CO_2$, another gas, or a mix of gases, depending on the intended use, flows into the inlet 102, through the body 140 and therefore through the metal-organic framework material 120, and out the outlet 104 carrying the one or more medicaments that were stored in the metal-organic framework material 120. The humidification system 108 can add humidity to the $CO_2$ and/or other gases passing through the container 100. The humidification system 108 can include, for example, a wicking material, a preloaded absorbent material, and/or a water reservoir and a heating plate.

The gases delivery system 290 (shown in FIGS. 5 and 6), including one or more of the container 100 comprising the metal-organic framework material 120, can further include a control system comprising a processor or controller. In some embodiments, the processor is disposed in the gases source 340. In other embodiments, the processor may be disposed in or co-housed with the container 100. The processor can receive user input from a user interface, for example, on the gases source 340 and/or the container 100. The user can manually enter operational parameters for the gases delivery system 290, the control system can automatically control the gases delivery system 290 based on pre-set operational parameters, or the control system can determine operational parameters based on a user selection or data input from the user. The control system can control the release of substances from the metal-organic framework material 120, for example, by controlling gases flow through the container 100 and/or the application of energy by the activation mechanism 110 to part or all of the container 100.

The gases delivery system 290 can also include various sensors to measure, for example, gas conditions such as flow rate, temperature, humidity, and/or pressure in the system. In some embodiments, it is beneficial to measure the temperature, humidity, and/or pressure of gases at or near the patient interface 360 or point of delivery to the patient. In some embodiments, measurements of properties of the gas flow at various points in the gases delivery system 290 can be used to estimate the values of those properties at other points in the gases delivery system 290. The data from various sensors can be sent to and received by the processor. The processor can use the sensor data as input to, for example, display information to the user via the user interface or determine operational parameters for the system to control the release of the one or more substances stored by the metal-organic framework material 120.

Preloading of the metal-organic framework material 120 can be achieved by directing a flow of one or more substances through the container 100, such that the metal-organic framework material 120 can selectively take up the one or more substances. In some embodiments, it may be desirable to provide the container 100 preloaded with one or more of a particular substance, such as water vapour and/or carbon dioxide. As an example, water vapour may be preloaded into the container 100 via a gases flow. If it is desirable to preload the metal-organic framework material 120 with only water vapour, a gas to which the metal-organic framework material 120 is not selective may be used as a carrier gas.

Figure 11:
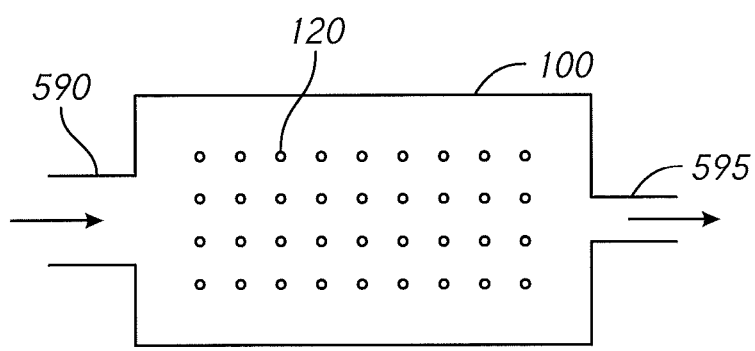
FIG. 11 is a schematic view of a container according to embodiments of the present disclosure.

Referring to FIG. 11, an example embodiment of the container 100 may comprise an inlet 590 and an outlet 595. The diameter of the inlet 590 may be larger than the diameter of the outlet 595, such that the one or more substances flowing through the container 100 are under pressure and are thus encouraged to be taken up by the metal-organic framework material 120. In some embodiments, a time period may be determined that indicates the amount of preloading and/or that sufficient preloading has taken place. In some embodiments, the measured pressure within the container 100 may be used as an indication of the amount of preloading that has occurred. In some embodiments, as described herein, the metal-organic framework material 120 may change color when a certain degree of preloading has been achieved. A housing or shell of the container 100, or a section therefore, can be transparent or at least partially transparent to allow the user to view such a color change. The inlet 590 and/or the outlet 595 may be closed following the preloading.

The container 100 as described may be used for a recirculation system, such that one or more substances may be initially preloaded into the metal-organic framework material 120 and then the recirculation system may cycle between release of the one or more substances from the metal-organic framework material 120 in use and storage of the one or more substances within the metal-organic framework material 120 during and/or following use. This cycle may repeat multiple times. In some embodiments, a filter may be positioned so as to filter the one or more substances, or other flow containing the one or more substances, before the one or more substances re-enter the container 100. In some embodiments, the container 100 may form a part of a recirculation system in, for example, laparoscopic surgery.

Figure 12:
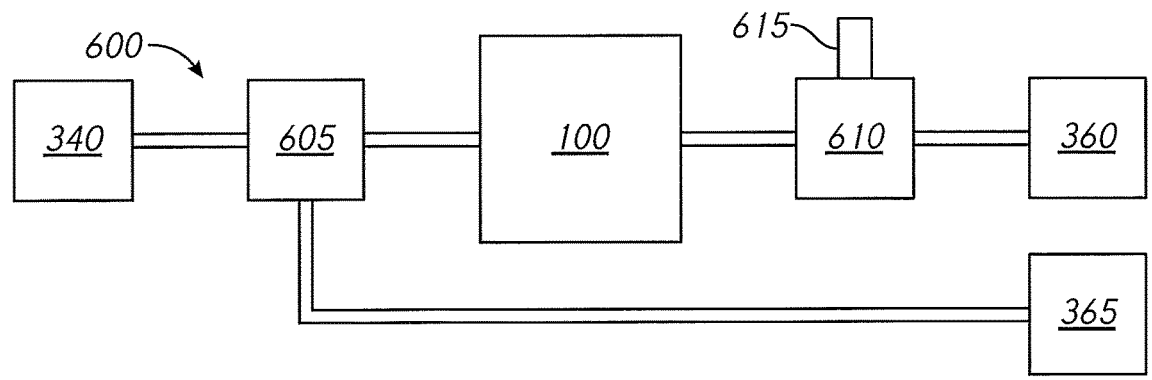
FIG. 12 is a schematic of a recirculation system comprising a container that comprises a metal-organic framework material according to an embodiment of the present disclosure.

FIG. 12 shows an example of a recirculation system 600 comprising the container 100. The recirculation system 600 may comprise a first pressure management system 605 configured to regulate the flow of recirculated gases from a gases recovery interface 365 into the container 100 and a second pressure management system 610 configured to ensure desired pressure levels of released gases at the patient interface 360. The first pressure management system 605 may also be configured to regulate the flow of gases from the gases source 340. The pressure management systems 605, 610 may comprise gases reservoirs, pressure regulators, valves, filters, and/or controllers and may coordinate with each other such that the container 100 alternates in function between supplying released gases and/or substances via the second pressure management system 610 and receiving recirculated gases via the first pressure management system 605. The second pressure management system 610 may comprise a vent 615 to allow excess gases to escape to the atmosphere. The first pressure management system 605 may comprise a similar vent (not shown).

Figure 13:
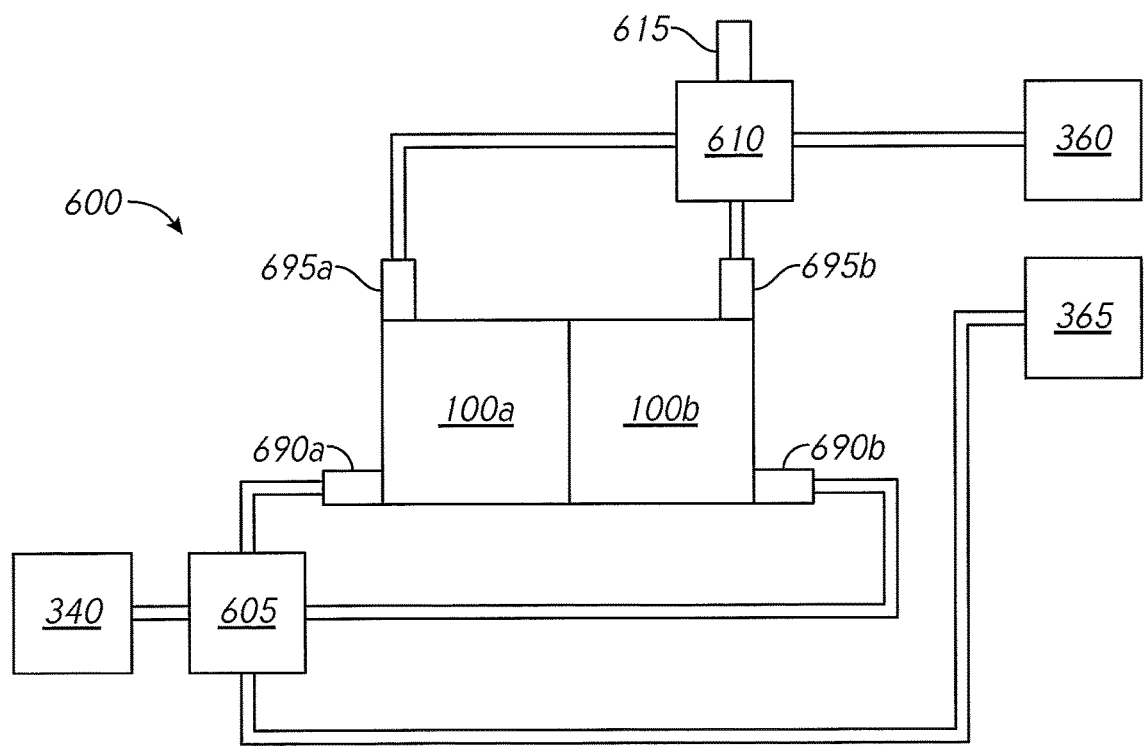
FIG. 13 is a schematic of a recirculation system comprising two containers that each comprise a metal-organic framework material according to an embodiment of the present disclosure.

FIG. 13 shows an example of the recirculation system 600 comprising two containers 100a, 100b. The recirculation system 600 may comprise the first pressure management system 605 and the second pressure management system 610 as described in relation to FIG. 12. The first pressure management system 605 may be configured to regulate the flow of recirculated gases from the gases recovery interface 365, and in some embodiments the flow of gases from the gases source 340, into either or both of the containers 100a, 100b via inlets 690a, 690b, respectively. The second pressure management system 610 may be configured to ensure desired pressure levels at the patient interface 360 of gases released from either or both of the containers 100a, 100b via outlets 695a, 695b, respectively. The pressure management systems 605, 610 may coordinate with each other such that the containers 100a, 100b alternate in function between one of the containers 100a, 100b supplying released gases and/or substances via the second pressure management system 610 and the other of the containers 100a, 100b receiving recirculated gases via the first pressure management system 605.

Figure 14:
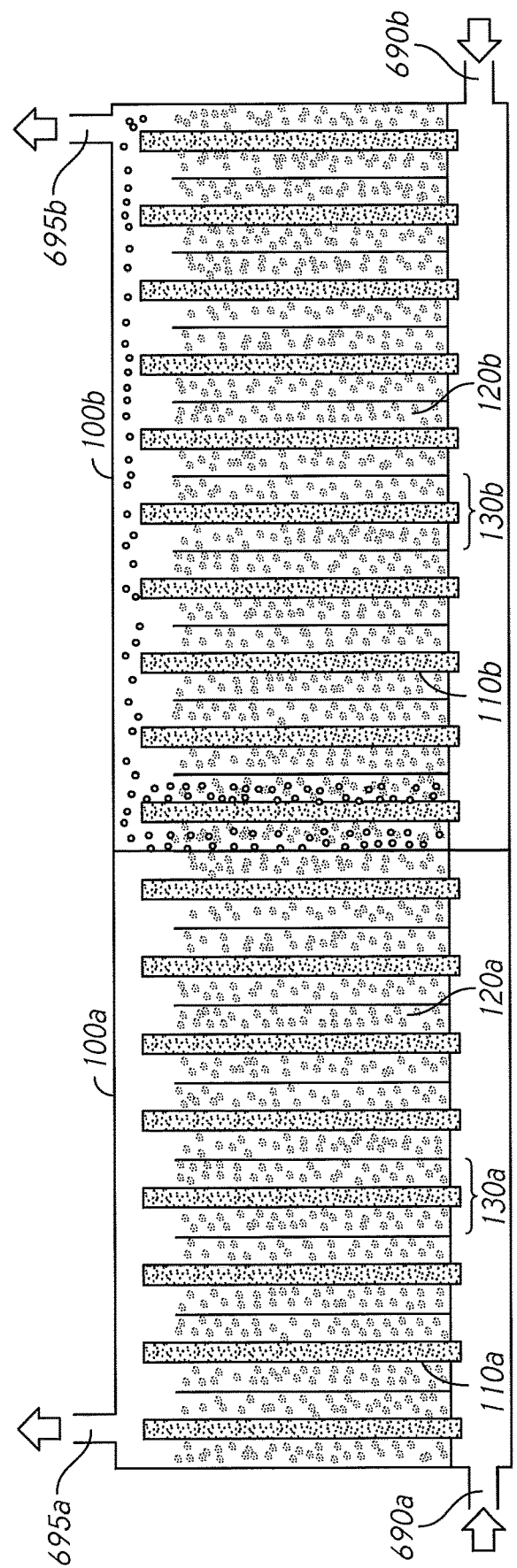
FIG. 14 is a cross-sectional top view of a container comprising a metal-organic framework material according to an embodiment of the present disclosure.

FIG. 14 shows the containers 100a, 100b of FIG. 13 in greater detail. A flow of recirculated gases comprising one or more substances, such as carbon dioxide and/or water vapour, may enter the first container 100a via the first inlet 690a. In some embodiments, the flow of recirculated gases may be delivered via the first pressure management system 605. A metal-organic framework material 120a may absorb the one or more substances entering the first container 100a such that the one or more substances are stored within the metal-organic framework material 120a. The flow of recirculated gases may exit the first container 100a via the first outlet 695a. In some embodiments, the flow of recirculated gases may then be delivered to the second pressure management system 610 and redirected therein to vent to the atmosphere through the vent 615. Storage of the one or more substances from the recirculated gases in the metal-organic framework material 120a may occur contemporaneously with release of one or more substances stored within a metal-organic framework material 120b in the second container 100b. In some embodiments, if external gases are used, such gases may be delivered to the second inlet 690b from the first pressure management system 605. Energy applied to the second container 100b via an activation mechanism 110b, either as a whole or differentially to one of sections 130b, may release the one or more substances stored within the second container 100b or the one of the sections 130b, via the second outlet 695b. In some embodiments, the released substances may then be delivered to the second pressure management system 610.

The first and second containers 100a, 100b may be configured to alternate in function such that, after a period of time, one or more stored substances are released from the first container 100a via the first outlet 695a by the application of energy via an activation mechanism 110a, either as a whole or differentially to one of the sections 130a, while one or more substances are stored in the second container 100b from a flow of recirculated gases entering the second container 100b via the second inlet 690b. The flow of recirculated gases may exit the second container 100b via the second outlet 695b. It is to be understood that a plurality of the first and second containers 100a, 100b may be used simultaneously and/or alternatively to provide a comprehensive recirculation system. The recirculation system 600 may be able to operate for longer periods of time or may be able to condition one or more substances at a rate desired by the user.

In some embodiments, the metal-organic framework material 120 may be recharged with one or more substances before, during, or after use. In some embodiments, the container 100 may be recharged a plurality of times.

The container 100 comprising the metal-organic framework material 120 may require preparation before it can be preloaded with one or more substances. The preparation may comprise applying energy, for example via the activation mechanism 110, such that the metal-organic framework material 120 releases any substances already stored therein. The container 100 may be sealed when not in use, for example using a cap or valve mechanism. Sealing may reduce the amount of substances inadvertently taken up by the metal-organic framework material 120 from the surrounding environment.

As previously described, in some embodiments, the activation mechanism 110 may be integral to the wall of the container 100. In other embodiments, the activation mechanism 110 may be located within the body 140 of the container 100. In an embodiment where the activation mechanism 110 is a heating mechanism, applying energy refers to heating the container 100, which may cause the one or more substances stored therein to be released. The rate of release of the one or more substances may be proportional to the amount of energy applied. Although some embodiments have been described as including a heating mechanism as the activation mechanism 110 for releasing substances stored in the metal-organic framework material 120, various embodiments according to the present disclosure can also or alternatively include other forms of the activation mechanism 110 that apply other forms of energy instead of or in addition to heat to release the stored substances.

The metal-organic framework material 120 may differ with regards to structure depending on the substances used. Some embodiments have been described with regards to use of carbon dioxide and/or water vapour, such as for use in a laparoscopic system. In other embodiments, the substance and/or the mixture of the substances used may comprise respiratory gases, for example oxygen, such that the disclosure can be used for a respiratory gases delivery system.

Other substances and/or uses are also possible. As examples of other substances and uses, the metal-organic framework material 120 according to the present disclosure can store and/or release anaesthetics; chemotherapy drugs (e.g., a combination of a platinum compound, such as cisplatin or carboplatin, and a taxane, such as paclitaxel or docetaxel), to be delivered to the peritoneum during cancer surgery; anti-adhesion agents (e.g., crystalloids, hyaluronic based solutions); vitamins (e.g., vitamins A, C, E), which can aid repair processes in the body; minerals; anti-inflammatory agents (e.g., all-trans-retinoic acid, quinacrine, dipyridamole); antibiotics (e.g., amoxicillin, maxacalcitol, cefuroxime), to help inhibit or reduce the likelihood of surgical site infections; integrin inhibitors (vitaxin, volociximab, intetumumab, resveratrol), to help reduce the likelihood of body tissues sticking to each other and/or other objects; pH altering chemicals (e.g., acids, bases), to increase acidity to increase local tissue oxygenation; anticoagulants (e.g., heparin); enzymes (e.g., super-oxide); biomarkers (e.g., fluorescein iso-thiocyanate with folate), to tag specific cells; radiation enhancers (e.g., combined fluorouracil and leucovorin), to aid or improve radiography; coagulants (e.g., adrenaline); vaso-constrictors (e.g., amphetamines, antihistamines, methylphenidate, mephedrone); and/or cardioplegia (e.g., calcium chloride, magnesium chloride, potassium chloride, sodium chloride), to reduce heart rate. In some embodiments, the metal-organic framework material 120 according to the present disclosure can be most useful for storing and/or releasing substances having a high boiling point. Such substances, such as medicaments, can therefore be turned into a vapour, taken up by the metal-organic framework material 120, and then released in a controlled manner.

The metal-organic framework material 120 according to the present disclosure can advantageously be used to deliver medicaments to a patient during surgery, including a laparoscopic procedure. Currently, aerosols may be delivered to the surgical space, such as the peritoneum. However, these aerosols have many drawbacks, and use of the metal-organic framework material 120 according to the present disclosure can overcome at least some of these disadvantages.

In some embodiments, the metal-organic framework material 120 comprises mmen-Mg2 or Cu-BTC. In some embodiments, the metal-organic framework material 120 that can be used in the devices and systems of the present disclosure is highly selective for $CO_2$ and $H_2O$.

The present disclosure may at least partially overcome or ameliorate at least one disadvantage of the prior art. Use of the metal-organic framework material 120 allows one or more substances to be stored in a solid form, which may allow the container 100 to be less vulnerable to changes in orientation, which may render it more portable and easier to transport than previous systems. In some cases, the container 100 may be preloaded when provided to a user such that the user has only to connect the container 100 to the gases delivery system 290 for use.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The apparatus and system of the disclosure may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the apparatus and systems of the disclosure and without diminishing its attendant advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

What is claimed is:

1. A gases delivery system for medical use comprising:
  a gases source configured to supply gases;
  a patient interface configured to be in fluid communication with the gases source and to deliver the gases to a patient;
  a container having an outlet configured to be in fluid communication with the patient interface and an inlet configured to be in fluid communication with the gases source, and a tube comprising a wall, the container configured to house a metal-organic framework material, the metal-organic framework material configured to store and release at least one substance, wherein the wall comprises at least a portion of the metal-organic framework material; and
  an energy source configured to apply energy to the metal-organic framework material to cause the metal-organic framework material to release the at least one substance to the gases.

2. The gases delivery system of claim 1, wherein the metal-organic framework material is preloaded with the at least one substance.

3. The gases delivery system of claim 1, wherein the metal-organic framework material is rechargeable with the at least one substance.

4. The gases delivery system of claim 1, wherein the at least one substance comprises one or more of water vapour, carbon dioxide, oxygen, nitrous oxide, argon, nitrogen, helium, or at least one medicament.

5. The gases delivery system of claim 1, wherein the metal-organic framework material comprises one or more of pellets, a powder, a mesh, a box, a monolith, or a lattice.

6. The gases delivery system of claim 1, wherein the gases source is integrated and/or co-located with the container.

7. The gases delivery system of claim 1, wherein the gases source is an external gas supply.

8. The gases delivery system of claim 7, wherein the external gas supply is configured to supply heated gases.

9. The gases delivery system of claim 7, wherein the external gas supply is configured to supply humidified gases.

10. The gases delivery system of claim 7, wherein the external gas supply is one of a gases canister, insufflator, ventilator, blower, or wall source.

11. The gases delivery system of claim 1, comprising a gas permeable membrane covering the inlet, the gas permeable membrane configured to prevent the metal-organic framework material escaping the container through the inlet.

12. The gases delivery system of claim 1, comprising a gas permeable membrane covering the outlet, the gas permeable membrane configured to prevent the metal-organic framework material escaping the container through the outlet.

13. The gases delivery system of claim 1, wherein the container comprises a plurality of sections, each section housing the metal-organic framework material or a different metal-organic framework material.

14. The gases delivery system of claim 13, wherein the plurality of sections comprises a first section and a second section, wherein the first section comprises the metal-organic frame material and the second section comprises the different metal-organic framework material.

15. The gases delivery system of claim 13, wherein each of the plurality of sections comprises the energy source or a different energy source.

16. The gases delivery system of claim 1, wherein the container comprises a transparent section.

17. The gases delivery system of claim 16, wherein the metal-organic framework material changes color in response to a change in a level of the at least one substance stored in the metal-organic framework material, and the transparent section allows a user to view changes in the color of the metal-organic framework material.

18. The gases delivery system of claim 1, wherein the energy source is configured to provide heat energy.

19. The gases delivery system of claim 1, wherein the energy source is configured to provide heat and vibration energy.

20. The gases delivery system of claim 1, wherein the energy source is a preheated gas flow directed into the container.

21. The gases delivery system of claim 1, wherein the container is configured to be disposed in-line between the gases source and the patient interface.

22. The gases delivery system of claim 1, wherein the container is configured to be coupled to the patient interface via a circuit, the circuit comprising a first end configured to be coupled to the outlet of the container and a second end configured to be coupled to the patient interface.

23. The gases delivery system of claim 1, wherein the gases source, patient interface, and energy source are arranged such that the gases are humidified prior to being delivered to the patient.

* * * * *